US00PP27838P2

(12) United States Plant Patent
Hansen

(10) Patent No.: US PP27,838 P2
(45) Date of Patent: Apr. 4, 2017

(54) ***HIBISCUS* PLANT NAMED 'MARS MADNESS'**

(50) Latin Name: ***Hibiscus* hybrid (L.)**
Varietal Denomination: Mars Madness

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 71 days.

(21) Appl. No.: 14/756,234

(22) Filed: Aug. 19, 2015

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Anne Grunberg

(57) ABSTRACT

A new and distinct cultivar of hardy herbaceous perennial *Hibiscus* hybrid plant named 'Mars Madness' comprising an upright dense branching, numerous flowers over a long season having vibrant magenta-red overlapping petals and a darker red lustrous eye halo. The foliage is dark-green with greyed-purple overlay, primarily heavily-dissected and tri-lobed.

1 Drawing Sheet

Botanical classification: *Hibiscus* hybrid (L.).
Variety denomination: 'Mars Madness'.

BACKGROUND AND ORIGIN OF THE PLANT

The present invention relates to the new and distinct hardy, herbaceous, *hibiscus* plant, *Hibiscus* 'Mars Madness' hybridized by the inventor on Jul. 27, 2011 at a nursery in Zeeland, Mich. The new plant is a single seedling selection from a cross between *Hibiscus* 'Crown Jewels' U.S. Plant Pat. No. 11,857 (female pod parent) times *Hibiscus* 'Midnight Marvel' U.S. Plant Pat. No. 24,079 (male pollen parent). The seed was harvested on Nov. 11, 2011 the specific seedling passed the initial trial in the summer of 2012 and eventually assigned the breeder code #11-117-8. Both parents have a complex mixture of species in them, most likely including the species: *moscheutos* and *coccineus*. *Hibiscus* 'Mission to Mars' was first asexually propagated in 2013 by both stem tip cuttings and sterile tissue culture at the same nursery in Zeeland, Mich. The resultant asexually propagated plants have been found to be stable and true to type in successive generations of asexual reproduction.

BRIEF SUMMARY OF THE PLANT

*Hibiscus* 'Mars Madness' differs from its parents as well as all other hardy herbaceous *hibiscus* known to the applicant in many traits. The foliage color of 'Mars Madness' is dark purplish-tinted green with generally ovate foliage. The most similar *hibiscus* in flower color known to the applicant is 'Sultry Kiss' U. S. Plant Pat. No. 22,300, but the new plant is shorter in habit, the flower is a deeper red color, and the foliage has more greyed-purple. Other similar *hibiscus* include: 'Carafe Yobordeaux' U.S. Plant Pat. No. 17,638, 'Cherry Brandy' U.S. Plant Pat. No. 18,944, 'Cinnamon Grappa' U.S. Plant Pat. No. 18,964, 'Cranberry Crush' U.S. Plant Pat. No. 21,984, 'Heartthrob' U.S. Plant Pat. No. 24,760, 'Midnight Marvel' U.S. Plant Pat. No. 24,079 and 'Vintage Wine' co-pending U.S. Plant patent application Ser.

No. 14/756,231. In comparison, 'Cranberry Crush' and 'Midnight Marvel' have a more cupped flower shape, more orange-red tinting of the petals, and are taller in habit than the new plant. 'Heartthrob' has a darker purple-red flower color and is taller and narrower in habit. 'Vintage Wine' is slightly darker purple-red in flower color, and has a more green ovate leaf shape. Compared to the female parent select, 'Crown Jewels', the new plant has a more upright dense habit with petals rather than nearly white petals.

Table 1 below outlines some of the comparisons of similar cultivars.

TABLE 1

| CULTIVAR | Leaf color | leaf shape | Flower color | Habit | Size (H × W) |
|---|---|---|---|---|---|
| 'Carafe Yobordeaux' | dark green | cordate to ovate | red purple | upright outward | 140 cm × 120 cm |
| 'Cherry Brandy' | green with some purple tinting | palmate | dark red | upright outward | 140 cm × 120 cm |
| 'Cinnamon Grappa' | green | palmate | red-purple | upright outward | 140 cm × 120 cm |
| 'Cranberry Crush' | dark green with purple overtones | ovate to tri-lobed | deep scarlet red | mound | 100 cm × 90 cm |
| 'Crowned Jewels' | green with greyed-purple tinting | tri-lobed | white with scarlet eye | open spreading | 105 cm × 200 cm |
| 'Heartthrob' | dark green | ovate to cordate | dark greyed-purple, blackish red eye | rounded mound | 100 cm × 140 cm |
| 'Mars Madness' | dark-green with purple overlay | tri-lobed | magenta red, darker halo eye and veins | broad mound | 135 cm × 180 cm |
| 'Midnight Marvel' | dark green, purple overlay | palmate | deep scarlet red, darker eye | mound | 85 cm × 80 cm |
| 'Vintage Wine' | dark green | ovate to cordate | scarlet red, darker eye | upright mound | 135 cm × 150 cm |

*Hibiscus* 'Mars Madness' is a unique hardy herbaceous hibiscus with the following combined traits:

1. Hardy perennial with dense branching and a compact, broad-mounded habit.
2. Many flowers over a prolonged season having vibrant magenta-red overlapping petals and a darker red lustrous halo eye and darker red veins.
3. Petals imbricate (overlapping) to 100% and slightly folded along veins providing additional strength to resist strong wind, bright sun and rain conditions.
4. Dark-green, greyed-purple, primarily tri-lobed foliage and contrasting light green calyxes.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
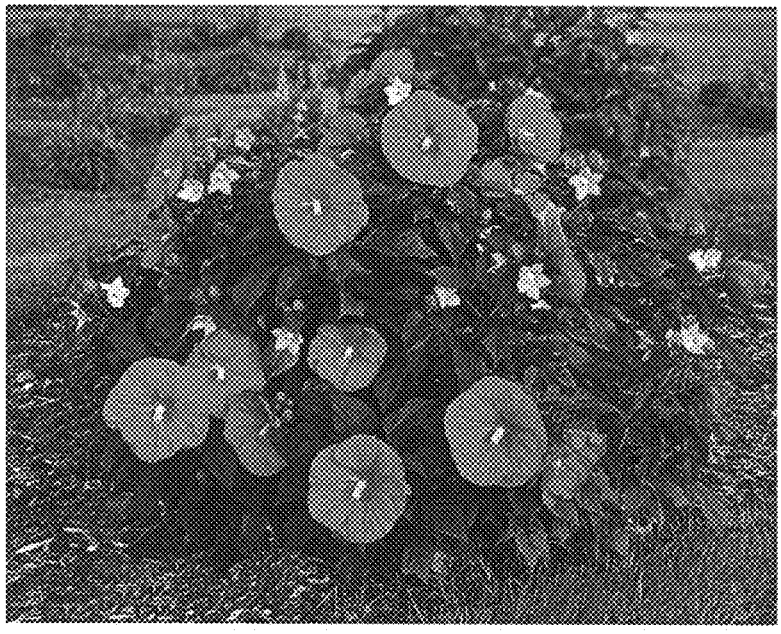
FIG. 1 shows a three-year old plant in the landscape with greyed-purple foliage, contrasting light green calyxes, and red flowers.
Figure 2:
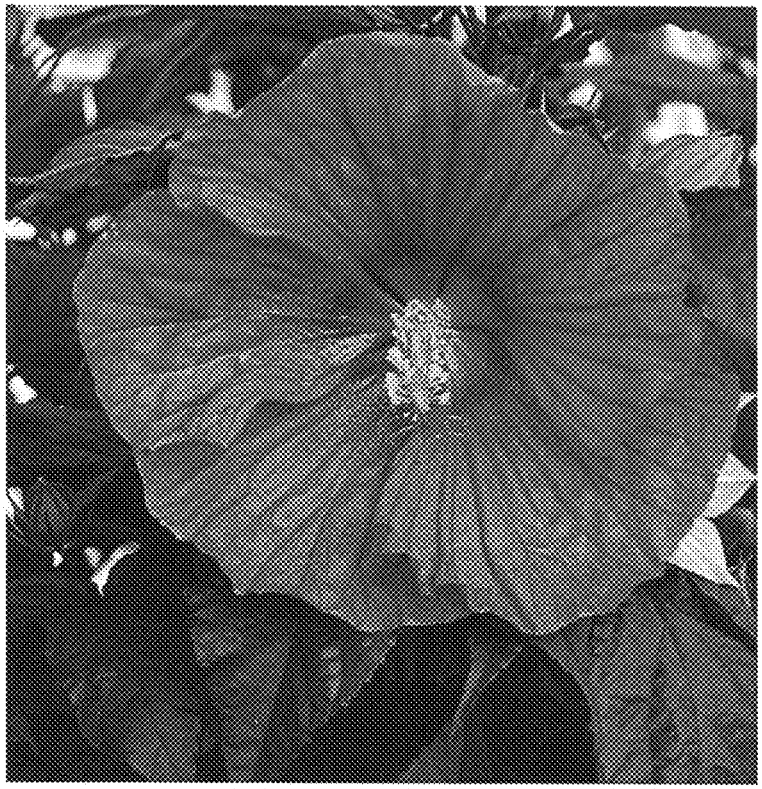
FIG. 2 shows a close-up of deep red flowers with deeper veins and halo eye.

The following descriptions and color references are based on the 2001 edition of The Royal Horticultural Society Colour Chart except where common dictionary terms are used. The new plant, *Hibiscus* 'Mars Madness', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand, open-field full-sun trials of a nursery in Zeeland, Mich. with supplemental fertilizer and water as needed. The plants are natural habit and were not treated with plant growth regulators, nor were they pinched at any time in the growth year.

Parentage: *Hibiscus* 'Crown Jewels' U.S. Plant Pat. No. 11,857 (female seed parent) times *Hibiscus* 'Midnight Marvel' U.S. Plant Pat. No. 24,079) (male pollen parent).

Propagation:

*Method*.—Stem cuttings and sterile plant tissue culture division.

*Time to initiate roots from tissue culture*.—About two weeks.

*Rooting habit*.—Normal, branching, developing thick to about 3.0 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant shape and habit*.—Hardy herbaceous perennial with 22 to 26 thick upright and heavily branched main stems producing a broad mound about 135.0 cm tall and 180.0 cm wide, widest about 100 cm above soil line; 10 to 19 primary lateral branches per main stem protruding at 80° to 60° angle from vertical in lower and outer, and 50° to 40° upper and inner branches, respectively, lateral branch size: between 8.0 cm and 21 cm long (shorter at the upper nodes) and average about 5.0 mm diameter at the base of branch; flowering on the upper ⅓ of the plant beginning at axillary nodes while still developing at the apex.

*Stem*.—Rounded, glabrous, glaucous; average about 130.0 cm tall and about 3.0 cm diameter at base; Stem color: nearest RHS 147D at base and nearest RHS 187C without glaucous bloom distally in more direct sunlight.

*Plant size*.—Unpinched plant with stems about 135 cm tall; overall plant about 180 cm wide about 35 cm from the top (widest point).

*Internode*.—About 30 nodes per stem before flowers, average internode length about 3.5 cm of unpinched plant, varied between about 2.0 cm to about 6.0 cm, widest in middle portion of stem.

Foliage description: Alternate; dentate; glabrous above and below; adaxial surface lustrous as expanding and matte when mature, abaxial matte; tri-lobed or ovate, rarely 5-lobed, incised nearly to petiole; with side lobes at about 60 degree angle from center lobe; apex of each lobe acute, base of blade flat to lightly cordate; texture above lustrous in distal leaves and matte in proximal leaves, texture below matte; center lobe to about 6.5 cm wide, side lobes to about 2.5 cm wide; total leaf blade size to about 20.0 cm long and about 18.0 cm wide, average about 16.0 cm long and about 14.0 cm wide, largest in center portion of stem.

*Foliage color*.—On young and mature leaves adaxial side base of nearest RHS 137A with greyed-purple between RHS 187A and RHS N137A when exposed to sufficient direct sunlight; abaxial young expanding and mature leaves nearest RHS 146B occasionally developing tinting of nearest RHS 187A.

*Veins*.—Palmate; glabrous adaxial and abaxial; adaxial nearly flat with leaf surface, abaxial rounded and protruding.

*Vein color*.—Adaxial primary and secondary veins between RHS 187B and RHS 187C on expanding and mature leaves, abaxial ranging between nearest RHS 184D on a background of nearest RHS 162D.

*Petioles*.—To about 14 cm long in lower leaves and about 6.0 mm wide; average size about 7.0 cm long and 4.0 mm wide; mostly cylindrical; slightly glaucous, glabrous.

*Petiole color*.—Adaxial nearest RHS 181B in more light and where protected from light nearest RHS 146C; abaxial nearest RHS 184B in more sun exposure and nearest RHS 146D where protected from high light intensities.

Flower description:

*Buds*.—One day prior to opening about 7.5 cm long and 5.5 cm in diameter, acute apex and bluntly rounded base, unopened petals wrinkled at veins.

*Bud color*.—Exposed petal color between RHS 59B and RHS 60A.

*Buds while petals still enclosed in sepals*.—About 3.5 cm long and 2.5 cm in diameter, ovoid with acute apex, carinate at the sepal fusion seams; main color between RHS 143C and RHS 144A with veining and sepal carina having tinting between RHS N187A and RHS 187A.

*Epicalyx*.—Entire, smooth, glabrous, linear with sharply acute apex and attenuate base, curved around sepals; typically 10 to 12 per flower; about 2.5 cm long and base of about 3.0 mm wide.

*Epicalyx color*.—Adaxial and abaxial main color RHS 143C and RHS 144A with tinting between RHS N187A and RHS 187A.

*Sepals*.—Five, proximal half connate forming campanulate star-shaped calyx; acute apex; margin entire, edentate; puberulent abaxial, glabrous adaxial; about 5.0 cm long and individually 2.5 cm wide at fusion point, 6.0 cm across together.

*Sepal color*.—Abaxial between RHS 143C and RHS 144A with tinting of between RHS N187A and RHS 187A; adaxial color between RHS 144B and RHS 143B.

*Flowers*.—Solitary, 50 to 58 per main stem including 2 to 6 per branch without pinching; petals opening to a flat face; slightly upward and outwardly facing; average 18.0 cm across and 5.0 cm deep, larger in early part of flowering season; persist for a one to two days; effective for at least 9 weeks beginning early August and lasting into October; no detectable fragrance.

*Petals*.—Five; glabrous, slightly lustrous in center and dull both front and back toward middle and perimeter, adnate to the androecium to form a column, imbricate to about 100% overlapping at widest part (petals completely overlapping the next petal to the petal in the position two over), palmately veined, primary and secondary veins impressed on front and ribbed on back; shape: rounded; margins: entire, edentate; apex: rounded; base: short claw-like; size: average about 8.5 cm long and about 12.0 cm wide at widest portion (largest in earlier part of flowering season); center dark eye halo about 5.0 cm diameter and 1.0 cm wide with a shiny center about 3.0 cm diameter.

*Petal color*.—Adaxial main color between RHS 60D and RHS 53C with a darker eye halo and veins nearest RHS 53A and tiny random flecks of about 2.5 mm long and 1.0 mm wide in the distal ⅓ between RHS 53B and RHS 53A; abaxial color nearest RHS 60D, abaxial vein color between RHS 53B and RHS 60C.

*Gynoecium*.—Style: enclosed in column about 6.5 cm long and about 1.2 cm wide at base; column color between RHS 61B and RHS 61C base, nearest RHS 61D distally; style protruding from column and split in distal 8.0 mm portion into typically five branches and protrudes from column, branch diameter 1.0 mm; branch color between RHS 60A and RHS 53A; Stigma: typically five; globose, puberulose, about 3.0 mm in diameter, color between RHS 60A and RHS 53A; Ovary: superior, about 6.0 mm across at base and 6.0 mm tall; acute apex; color between RHS 145B and RHS 145C.

*Androecium*.—Filaments: numerous, about 120; less than 0.5 mm in diameter and about 4.0 mm long; attached along nearly the entire length of column from base to apex; color nearest RHS 61D; Anthers: reniform; about 2 mm long and 1 mm wide; color nearest RHS 182C; Pollen: numerous, globose, less than 0.1 mm long, between RHS 155A and RHS 158A.

*Pedicel*.—Rounded in cross section, glabrous; length from flower base of sepal to abscission point average 1.5 cm long and 3.0 mm wide, longer on early flowers decreasing in distal flowers; color nearest RHS 182C.

*Peduncle*.—Rounded, glabrous, flowers are held easily visible on average 4.0 cm long from abscission point to stem and 3.0 mm wide, longer on earlier flowers; color nearest RHS 184B.

*Fruit*.—Few, loculicidal capsule; glabrous; globose, occasionally with abruptly acute apex; color between RHS N199B and RHS N199C when mature.

*Seed*.—Minutely floccose, typically globose; about 3.0 mm in diameter; color between RHS 200A and RHS N199B.

Resistance: The flowers of 'Mars Madness' have resisted wind, rain and hot sun conditions better than many hardy perennial *hibiscus*. Other pest and disease resistance beyond that of other hardy perennial *hibiscus* cultivars has not been observed. The plant grows best with plenty of moisture, but is able to tolerate some drought once established. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Mars Madness' as herein illustrated and described.

* * * * *